(12) United States Patent
Wang et al.

(10) Patent No.: US 10,828,271 B2
(45) Date of Patent: Nov. 10, 2020

(54) METHOD FOR TREATING PLEUROPERITONEAL MEMBRANE CANCERS BY LOCALLY INJECTING DISULFIRAM PREPARATION

(71) Applicant: NUOMA (BEIJING) TECHNOLOGY CO., LTD, Beijing (CN)

(72) Inventors: Weiguang Wang, Wolverhampton (GB); Zhipeng Wang, Xi'an (CN)

(73) Assignee: UNIVERSITY OF WOLVERHAMPTON, Wolverhampton (GB)

( * ) Notice: Subject to any disclaimer, the term of this patent is extended or adjusted under 35 U.S.C. 154(b) by 99 days.

(21) Appl. No.: 16/093,187

(22) PCT Filed: Apr. 13, 2017

(86) PCT No.: PCT/CN2017/080463
§ 371 (c)(1),
(2) Date: Oct. 12, 2018

(87) PCT Pub. No.: WO2017/177947
PCT Pub. Date: Oct. 19, 2017

(65) Prior Publication Data
US 2019/0117595 A1    Apr. 25, 2019

(30) Foreign Application Priority Data
Apr. 13, 2016 (CN) .......................... 2016 1 0228576

(51) Int. Cl.
| | | |
|---|---|---|
| A61K 31/27 | (2006.01) | |
| A61K 31/145 | (2006.01) | |
| A61K 33/34 | (2006.01) | |
| A61K 45/06 | (2006.01) | |
| A61P 35/00 | (2006.01) | |
| A61K 31/30 | (2006.01) | |

(52) U.S. Cl.
CPC ............ *A61K 31/145* (2013.01); *A61K 31/30* (2013.01); *A61K 33/34* (2013.01); *A61K 45/06* (2013.01); *A61P 35/00* (2018.01)

(58) Field of Classification Search
CPC ..................................................... A61K 31/27
USPC ........................................................ 514/476
See application file for complete search history.

(56) References Cited

U.S. PATENT DOCUMENTS
| | | |
|---|---|---|
| 6,288,110 B1 | 9/2001 | Marikovsky |
| 2010/0196436 A1 | 8/2010 | Gooberman |
| 2014/0037715 A1 | 2/2014 | Wang |
| 2018/0311178 A1 | 11/2018 | Wang et al. |

FOREIGN PATENT DOCUMENTS
| | | |
|---|---|---|
| CN | 102274347 A | 12/2011 |
| CN | 102357100 A | 2/2012 |
| CN | 103221040 A | 7/2013 |
| CN | 105125495 A | 12/2015 |
| CN | 106377496 A | 2/2017 |
| WO | WO-2008/068746 A2 | 6/2008 |
| WO | WO-2015/120254 A1 | 8/2015 |

OTHER PUBLICATIONS

Chun, "What are the most curable cancers?," Medical News Today, <https://www.medicalnewstoday.com/articles/322700.php>, retrieved Jul. 19, 2019 (4 pages).
Extended European Search Report for European Patent Application No. 17781923.2, dated Nov. 27, 2019 (8 pages).
Faiman et al., "Disulfiram distribution and elimination in the rat after oral and intraperitoneal administration," Alcohol Clin Exp Res. 4(4):412-9 (1980).
International Search Report for International Patent Application No. PCT/CN2017/080463, dated Jul. 14, 2017 (9 pages).
Makadia et al., "Poly Lactic-co-Glycolic Acid (PLGA) as Biodegradable Controlled Drug Delivery Carrier," available in PMC May 8, 2012, published in final edited form as: Polymers (Basel). 3(3):1377-97 (2011) (19 pages).
Muthu, "Nanoparticles based on PLGA and its co-polymer: an overview," Asian J Pharm. 3(4): 266-73 (2009).
Panyam et al., "Solid-state solubility influences encapsulation and release of hydrophobic drugs from PLGA/PLA nanoparticles," J Pharm Sci. 93(7):1804-14 (2004).
Skrott et al., "Alcohol-abuse drug disulfiram targets cancer via p97 segregase adaptor NPL4," Nature. 552(7684):194-9 (2017) (23 pages).
Cheriyan et al. "Disulfiram suppresses growth of the malignant pleural mesothelioma cells in part by inducing apoptosis," PLoS One. 9(4):e93711 (2014) (14 pages).
Fasehee et al., "The inhibitory effect of disulfiram encapsulated PLGA NPs on tumor growth: Different administration routes," Mater Sci Eng C Mater Bio Appl. 63:587-95 (2016).
Hoda et al., "Anti-proliferative and apoptosis-triggering potential of disulfiram and disulfiram-loaded polysorbate 80-stabilized PLGA nanoparticles on hepatocellular carcinoma Hep3B cell line," Nanomedicine. 12(6):1641-50 (2016).
Hoda et al., "Influence of stabilizers on the production of disulfiram-loaded poly(lactic-co-glycolic acid) nanoparticles and their anticancer potential," Ther Deliv. 6(1):17-25 (2015).
Ketola et al., "Chemical Biology Drug Sensitivity Screen Identifies Sunitinib as Synergistic Agent with Disulfiram in Prostate Cancer Cells," PLoS One. 7(12):e51470 (2012) (11 pages).
Löbler et al., "Drug delivery by nanoparticles—facing the obstacles," IFMBE Proceedings. 22:2335-2338 (2009).
Phillips et al., "Sustained-release characteristics of a new implantable formulation of disulfiram," J Pharm Sci. 73(12):1718-20 (1984).
Song et al., "Stable loading and delivery of disulfiram with mPEG-PLGA/PCL mixed nanoparticles for tumor therapy," Nanomedicine. 12(2):377-86 (2016).

*Primary Examiner* — Ramond J Henley, III
(74) *Attorney, Agent, or Firm* — Clark & Elbing LLP

(57) ABSTRACT

The present invention provides a method for treating pleuroperitoneal membrane cancers, and comprises: delivering disulfiram or a derivative thereof that is effective in amount in the treatment, into the pleura and/or the peritoneum of a test person that needs to be treated. The present invention also provides a pharmaceutical component comprising the disulfiram or the derivative thereof, and a reagent kit.

10 Claims, 10 Drawing Sheets

METHOD FOR TREATING PLEUROPERITONEAL MEMBRANE CANCERS BY LOCALLY INJECTING DISULFIRAM PREPARATION

TECHNICAL FIELD

The present invention relates to the field of cancer treatment, and in particular relates to a method for treating primary as well as metastatic pleuroperitoneal membrane cancer via local injection of a disulfiram preparation.

BACKGROUND ART

Disulfiram has been used in the treatment of alcoholism for more than 60 years (Johansson, 1992). Disulfiram is sensitive to ethanol, with patients developing an uncomfortable response even if they ingest a small amount of ethanol during treatment. Disulfiram inhibits the activity of aldehyde dehydrogenase (ALDH) and blocks the oxidation of ethanol at the acetaldehyde stage. Thus, after ingestion of disulfiram, the concentration of acetaldehyde in human blood is 5 to 10 times higher than that of acetaldehyde in subjects who have consumed an equivalent amount of ethanol without taking disulfiram. The accumulation of acetaldehyde in the blood produces extreme discomfort, referred to as a disulfiram-ethanol reaction, which is proportional to the amount of disulfiram and ethanol ingested, and said reaction persists until all the ethanol present in the body is metabolized. Even when taken with a small amount of ethanol, disulfiram can still cause facial flushing, severe pulsation of the blood vessels of the head and neck, pulsating headache, difficulty breathing, nausea, vomiting, sweating, dry mouth, chest pain, palpitations, hyperventilation, tachycardia, hypotension, syncope, restlessness, fatigue, dizziness, blurred vision and paralysis.

Experiments conducted in vitro have shown that disulfiram is highly cytotoxic to a variety of cancer cells (Wang, et al., 2003, Cen, et al., 2004, Liu, et al., 2012, Yip, et al., 2011, Liu, et al., 2014). The effective concentration of disulfiram with respect to tumor cells corresponds to the nanomolar range, and the drug shows a more significant in vitro anticancer effect when compared to many anticancer drugs used in clinical practice (such as daunorubicin, 5-fluorouracil, gemcitabine, paclitaxel, platinum-based agents, vinblastine, etc.). Although the results of in vitro experiments have been very encouraging, very few studies have reported the anticancer activity of disulfiram in animal experiments. Moreover, currently all prototypical anti-cancer experiments which examine disulfiram in animals require a very high dose of disulfiram to produce limited anticancer effects in mice (Iljin, et al., 2009, Brar, et al., 2004, Chen, et al., 2006). The dose used causes damage to the vital organs (lungs, liver, kidneys, etc.). Therefore, clinical cancer patients are not able to tolerate said dose. There are currently several clinical trials pertaining to the treatment of cancer with disulfiram that have been completed or are in progress [(Stewart, et al., 1987, Verma, et al., 1990) ClinicalTrials.gov: NCT00256230, NCT00742911, NCT01118741], but the results of these trials have yet to be reported. The differences in data obtained in in vitro, in vivo and clinical studies support the conclusion that oral disulfiram formulations are not suitable for the treatment of cancer in human patients.

Therefore, as of now, disulfiram has not been used as an anticancer drug in humans due to the fact that potential clinical application of disulfiram in the treatment of cancer is not feasible given the limitations of existing oral preparations of disulfiram. After oral administration, disulfiram is extremely unstable in gastric acid, and most oral disulfiram rapidly decomposes into carbon disulfide ($CS_2$) and diethylamine (DEA) (Johansson, 1992). Absorbed disulfiram reacts with the thiol groups of serum albumin in the bloodstream, after which it is rapidly reduced by the glutathione reductase system in the red blood cells (half-life: 4 minutes) and rapidly converted to diethyldithiocarbamate (DDC, also referred to as diethyldithiocarbamic acid). The vast majority of orally absorbed disulfiram and its derivatives are enriched by the liver. Sulfhydryl groups in DDC and disulfiram molecules are rapidly methylated or glucuronidated in the liver to form methyl DDC and glucuronic acid DDC (Agarwal, et al., 1983, Agarwal, et al., 1986, Gessner and Jakubowski, 1972, Kaslander, 1963, Prickett and Johnston, 1953). Our unpublished data confirm that both metabolites completely lack any anticancer activity. Therefore, an oral dose of 500 mg of disulfiram produces a blood concentration below the detection limit. Note that the above reactions do not affect the anti-alcoholism effects of disulfiram. Because the liver is an alcohol-metabolizing organ, oral disulfiram is rapidly methylated and accumulates in the liver, and methylated disulfiram has a strong inhibitory effect on ALDH. Our experiments demonstrate that disulfiram is a divalent metal ion chelating agent that produces a large amount of reactive oxygen species (ROS) when chelated with copper ions and other divalent metal ions. ROS are highly lethal against cancer cells. However, ROS have a very short life (measured in nanoseconds) in bodily fluids. Therefore, disulfiram and copper ions must produce a chelation reaction in cancer tissues in order to kill cancer cells (Tawari, 2015). The final product formed by disulfiram and copper ions, copper diethyldithiocarbamate, also produces a lethal effect on cancer cells. Whether in the chelation reaction itself or the formation of the final product, the thiol group (—SH) present in the disulfiram molecule is indispensable. However, the sulfhydryl groups of disulfiram are destroyed during methylation and glucuronidation, thus removing the molecule's ability to produce reactive oxygen species and copper diethyldithiocarbamate. Our unpublished experimental data demonstrate that methylated disulfiram completely loses its anticancer activity. The fact that disulfiram is rapidly metabolized and degraded in the blood poses a serious challenge to clinical anticancer applications of disulfiram and explains the unsatisfactory results obtained in clinical trials (www.clinicaltrials.gov/). Differences in data obtained from in vitro cytotoxicity testing and anticancer effects observed in actual patients indicate that the administration of disulfiram via the gastrointestinal system does not deliver a therapeutic dose of the drug to the cancer site due to rapid transformation and degradation in the gastrointestinal tract and blood, the transhepatic first-pass effect and intrahepatic transformation and degradation, and is therefore a major limiting factor in the clinical use of disulfiram for cancer treatment.

SUMMARY OF THE INVENTION

In view of the strong anticancer activity of disulfiram in vitro as well as its ultrashort blood half-life severely limiting its clinical anticancer application, in the present invention we used local administration of disulfiram to carry out local treatment of pleuroperitoneal membrane cancer, thereby overcoming the bottleneck of disulfiram's short half-life.

The present invention provides a method of treating primary or metastatic pleuroperitoneal membrane cancer which includes the intra-pleuroperitoneal administration of an effective dose of disulfiram or a derivative thereof to a subject requiring treatment.

The present invention also provides the use of disulfiram or a derivative thereof in the preparation of a drug for the treatment of pleuroperitoneal membrane cancer in a subject via intra-pleuroperitoneal administration.

The present invention also provides an effectively deliverable preparation of disulfiram or a derivative thereof, wherein intra-pleuroperitoneal administration is performed to treat a subject's pleuroperitoneal membrane cancer.

The present invention also provides a disulfiram or derivative thereof for treating the pleuroperitoneal membrane cancer of a subject via intra-pleuroperitoneal administration.

In a particularly preferred embodiment, the present invention also provides methods for the combined and non-combined administration of disulfiram or a derivative thereof (such as DDC) serving as an active ingredient and copper, zinc, iron, gold or another divalent transition metal element. For example, in a particular embodiment of the present invention, disulfiram or a derivative thereof (such as DDC) may be administered via the pleuroperitoneal cavity while copper, zinc, iron, gold or another bivalent transition metal element is administered orally or via the pleuroperitoneal cavity, either simultaneously or at a different time, in order to treat a subject's pleuroperitoneal membrane cancer. The present invention also provides an application in which disulfiram or a derivative thereof (such as DDC) is administered either in combined or non-combined form with copper, zinc, iron, gold or another bivalent transition metal element in combination with an existing anticancer drug to treat pleuroperitoneal membrane cancer, thereby increasing the anticancer activity of existing anticancer drugs and/or lessening the toxic side effects of existing anticancer drugs.

The invention also provides a kit comprising: (1) disulfiram or a derivative thereof as a therapeutic agent; and (2) instructions for use, wherein said instructions describe the use of disulfiram or a derivative thereof for the treatment of a subject's pleuroperitoneal membrane cancer via intra-pleuroperitoneal administration.

In contrast, 60% of mice in the DS/Cu treatment group survived up to Day 90. The above difference was significant (P=0.016).

Figure 13:
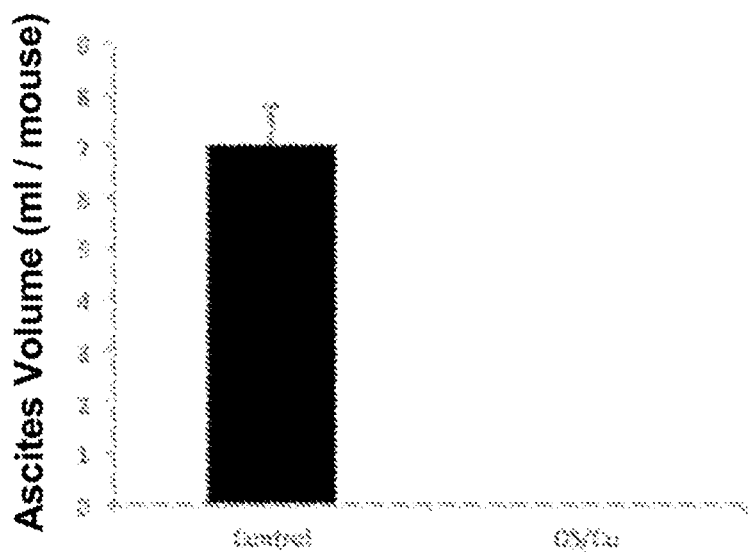

FIG. 13: Comparison of ascites volume. After intraperitoneal injection of MSTO mesothelioma cells in CD1 nude mice, significant ascites was observed in mice belonging to the control group by Day 60, but no significant ascites was observed in the DS/Cu treatment group (as of Day 90).

Figure 14:
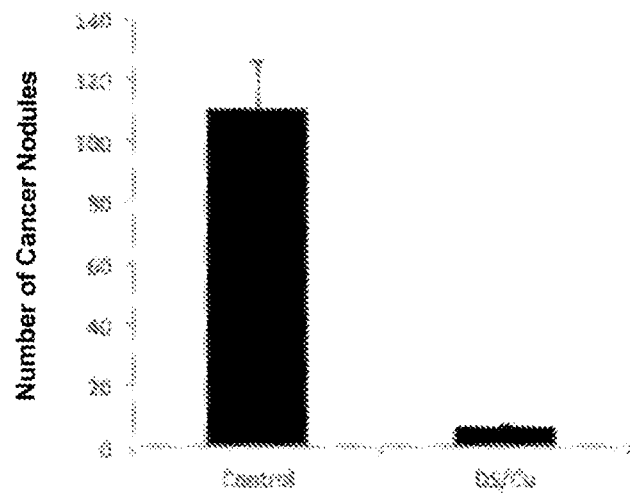

FIG. 14: Comparison of cancer nodule number. After intraperitoneal injection of MSTO mesothelioma cells in CD1 nude mice, the number of cancer nodules observed in the control group by Day 60 was significantly higher than in the DS/Cu treatment group (as of Day 90). P<0.01.

Figure 15:
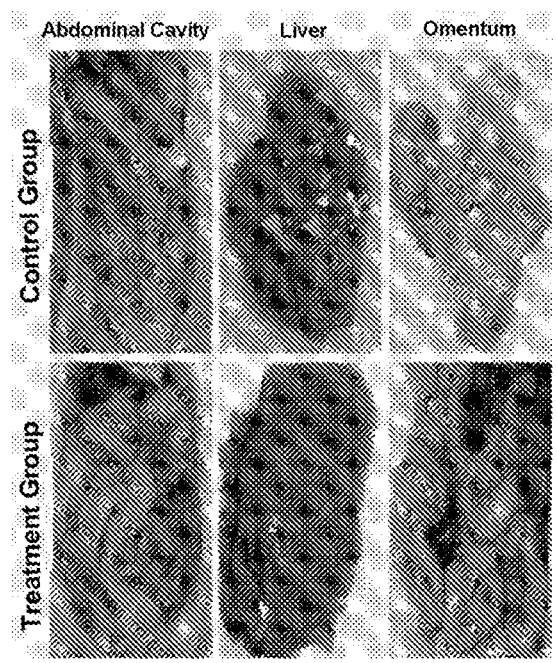

FIG. 15: This figure shows a peritoneal cancer nodule. After injection of MSTO mesothelioma cells in CD1 nude mice, a large number of cancer nodules were observed in the control group by Day 60. Multiple masses (indicated by arrows) were clearly visible in the abdominal wall, liver and mesentery. Mice in the DS/Cu treatment group showed a clean abdominal cavity with almost no cancer nodules.

Figure 16:
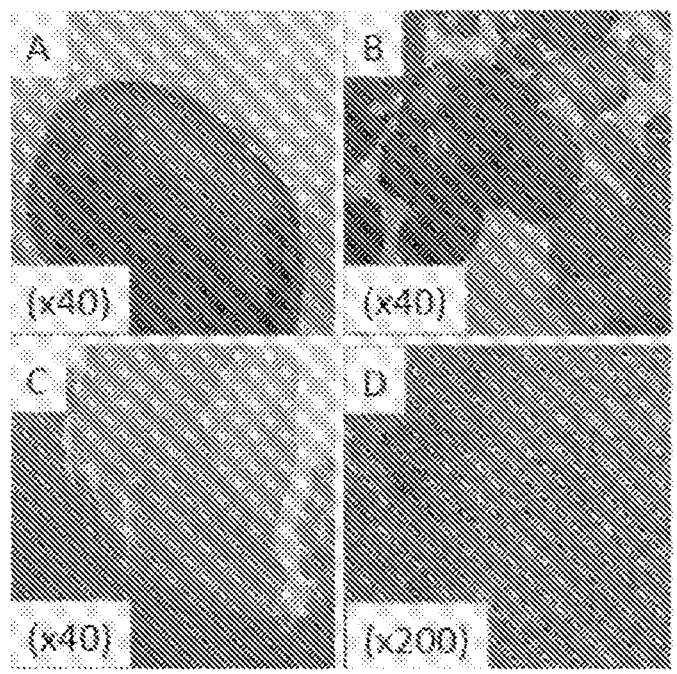

FIG. 16: Pathology images of cancer nodules. A. Mesenteric invasion. B. Intra-abdominal nodules. C. Liver invasion. D. High power field of view.

Figure 17:
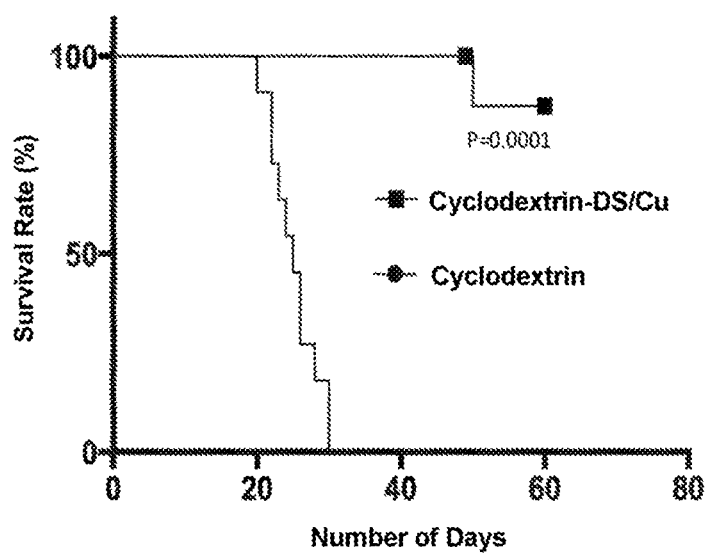

FIG. 17: This figure shows mouse survival. After CD1 nude mice were injected intraperitoneally with ovarian cancer cells, all mice in the control group died by Day 30. In contrast, 90% of mice in the DS/Cu treatment group survived up to Day 60. P=0.0001, n=10.

Figure 18:
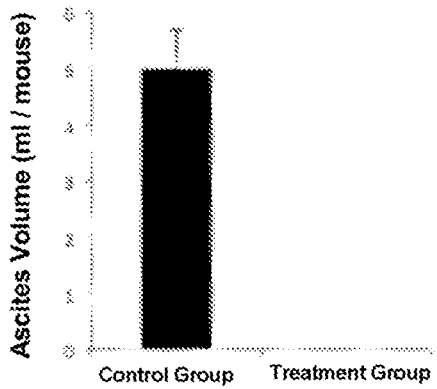

FIG. 18: Comparison of ascites volume. After intraperitoneal injection of ovarian cancer cells in CD1 nude mice, significant ascites was observed in mice belonging to the control group by Day 30, but no significant ascites was observed in the DS/Cu treatment group (as of Day 60).

Figure 19:
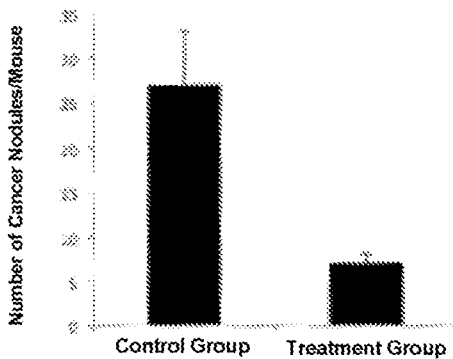

FIG. 19: Comparison of cancer nodule number. After injection of ovarian cancer cells in CD1 nude mice, a large number of cancer nodules were observed in the control group by Day 30. On Day 60, the number of intraperitoneal nodules observed in mice in the DS/Cu treatment group was significantly lower than the control group. P<0.01, n=10.

Figure 20:
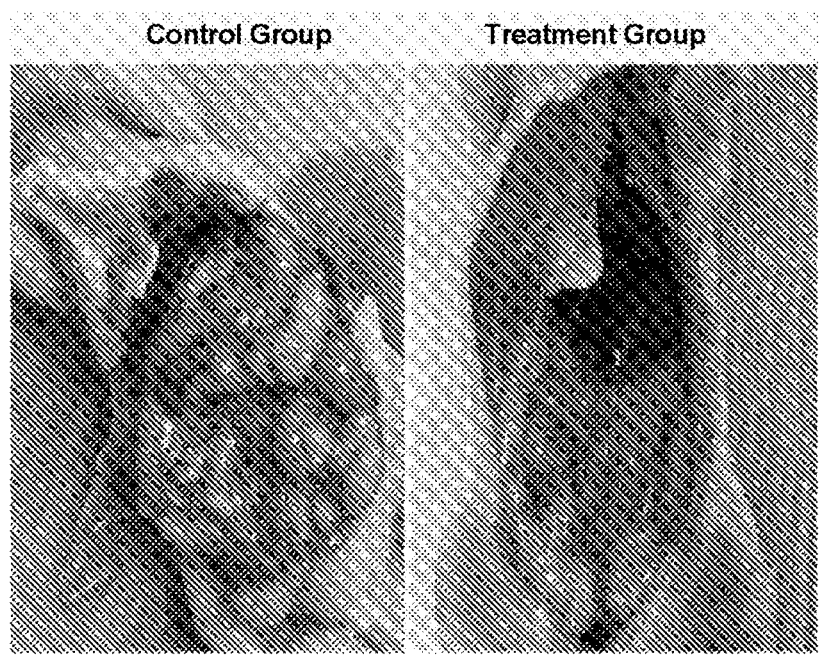

FIG. 20: This figure shows a peritoneal cancer nodule. After injection of ovarian cancer cells in CD1 nude mice, a large amount of cancer nodules was observed in the control group by Day 30. Multiple masses were clearly visible in the abdominal wall and mesentery. Mice in the DS/Cu treatment group showed a clean abdominal cavity with fewer cancer nodules (Day 60).

SPECIFIC EMBODIMENTS

In their experiments, the inventors of the present invention discovered that disulfiram produces a strongly lethal effect on human malignant mesothelioma and ovarian cancer cell lines in vitro, and disulfiram can synergistically enhance the lethality of pemetrexed and cisplatin against mesothelioma and ovarian cancer cell lines in humans in vitro. Given that local application of disulfiram in the pleuroperitoneal cavity can overcome the bottleneck constituted by the drug's short half-life, the inventors of the present invention performed intraperitoneal injection of disulfiram (5 mg/kg) as well as simultaneous oral administration of copper gluconate in S180 sarcoma tumor-bearing mice, and were thereby able to completely eliminate the animals' peritoneal metastasis. The above dose is only approximately ⅛ of a typical dose of disulfiram used to treat alcoholism (250 mg/person/day; human:mouse=1:9). This exciting result prompted the inventors of the present invention to further perform experiments pertaining to the treatment of human peritoneal mesothelioma and ovarian cancer. In further experiments, the inventors of the present invention used only 1/20 of a typical dose of disulfiram used to treat alcoholism (2 mg/kg) to achieve 60% and 90% long term survival in peritoneal mesothelioma and ovarian cancer mice (90 and 60 days).

The above finding is quite exciting taking into consideration the results of past research.

Without being bound by any particular theory, the inventors of the present invention believe that the above results may be attributable to the fact that direct delivery of disulfiram to the vicinity of the tumor tissue when intraperitoneal injection of disulfiram is performed overcomes the disadvantages of other modes of administration such as oral and intravenous injection, namely rapid metabolism and degradation of disulfiram in the gastrointestinal system and blood circulation, and the above method is also beneficial in that it allows disulfide to rapidly react with divalent copper ions permeating into the peritoneal fluid through the blood circulation after oral administration to produce a cytotoxic effect on cancer cells in the abdominal cavity. Thus, the present invention provides a method of treating pleuroperitoneal membrane cancer which includes the intrapleural and/or intraperitoneal administration of an effective dose of disulfiram or a derivative thereof to a subject requiring treatment.

As used herein, the term "intrapleural administration", also referred to as "pleural administration" or "intrathoracic administration", refers to the delivery of a drug through the pleura into the pleural cavity.

As used herein, the term "intraperitoneal administration", also referred to as "intraperitoneal cavity administration", "peritoneal administration" or "parenteral administration", refers to the delivery of a drug through the peritoneum into the peritoneal cavity.

As used herein, the term "intra-pleuroperitoneal administration" refers to the delivery of a drug through the pleura or peritoneum into the pleural cavity or peritoneal cavity. Those skilled in the art will appreciate that intrapleural and intraperitoneal administration can be performed simultaneously under certain circumstances, such as when cancer designated for treatment is present in both the pleura and the peritoneum. The term "intra-pleuroperitoneal administration" also encompasses simultaneous administration to the pleural and peritoneal cavities. "Intra-pleuroperitoneal administration" has the same meaning as "intrapleural and/or intraperitoneal administration."

After being delivered into the chest or abdominal cavity, disulfiram or a derivative thereof can rapidly spread to tumor tissue through pleural effusion or ascites, thereby producing an anticancer effect.

Intra-pleuroperitoneal administration can be conveniently performed via syringe, peristaltic pump or pleuroperitoneal catheter.

As used herein, the term "cancer" includes any suitable type of cancer, such as malignant mesothelioma, gastric cancer, kidney cancer, bladder cancer, ovarian cancer, breast cancer, endometrial cancer, pancreatic cancer, lymphoma, thyroid cancer, bone cancer, central nervous system cancer, leukemia, liver cancer, prostate cancer, lung cancer, colon cancer, rectal cancer, brain cancer and melanoma, as well as human and animal malignancies that have previously been or are not currently reported. As used herein, the term "pleural and/or peritoneal carcinoma" refers to any malignant tumor that grows in the pleura and/or peritoneum of a patient, including primary pleuroperitoneal membrane cancer as well as pleuroperitoneal membrane metastases.

Here, primary pleuroperitoneal membrane cancer includes malignant mesothelioma and any other type of malignant tumor that originates in the pleuroperitoneal membrane. The method constituted by the present invention is particularly well-suited to the treatment of malignant mesothelioma.

Malignant mesothelioma is a rare type of tumor that occurs in the pleura and peritoneum, and onset is closely related to asbestos exposure.

Malignant pleural mesothelioma is the most common type of primary pleural tumor encountered in clinical practice. Clinical manifestations are associated with the tumor's invasive behavior as it locally invades the pleural cavity and surrounding structures. If the condition is left untreated, median survival is 4 to 12 months.

Here, pleuroperitoneal membrane metastasis refers cancer that migrates to the pleura and/or peritoneum from other parts of the body. The condition primarily includes gastric cancer, ovarian cancer, pancreatic cancer, lymphoma, leukemia, liver cancer, lung cancer, colorectal cancer, or any other metastatic cancer.

The method constituted by the present invention is particularly well-suited to the treatment of peritoneal metastatic cancer. The most common forms of peritoneal metastatic cancer include ovarian cancer, pancreatic cancer, liver cancer, stomach cancer, colorectal cancer, and any other cancer that metastasizes to the peritoneum. Peritoneal metastases were previously regarded as a terminal stage of cancer. Supportive care, systemic chemotherapy and palliative surgery are largely ineffective in extending patient survival.

The peritoneal metastasis rates for gastric cancer, ovarian cancer, pancreatic cancer, and colon cancer are 99%, 90%, 50%, and 32%, respectively, due to the locations of the affected organs. Additionally, cancer of other organ systems can also produce distal metastasis and spread to the peritoneum, including breast cancer, lung cancer and lymphoma.

The pharmaceutical preparation constituted by the present invention can be used to prevent and/or inhibit the proliferation of tumor cells and/or tumor stem cells. The ineffectiveness of cancer treatments against cancer stem cells is thought to be the cause of many cancer treatment failures.

As used herein, the term "treatment" refers to the management and care of a patient to combat a disease or disorder. The term includes broad-spectrum treatments for a particular condition, such as administration of an active compound to alleviate symptoms or complications, delay progression of a disease, alleviate or ameliorate symptoms and complications or cure or eliminate a disease or condition, and also includes the prevention of said disease or condition. Subjects to be treated preferably correspond to a type of mammal, including especially humans, but also including animals such as dogs, cats, horses, cows, sheep and pigs.

Disulfiram and its Derivatives

The chemical structure corresponding to the term "disulfiram" (DS) as used herein is as follows:

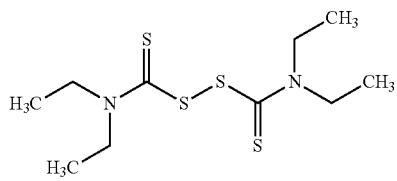

Derivatives of disulfiram can be represented by the following chemical structural formula:

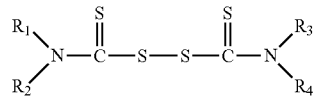

The basic structure corresponds to thiuram disulfide. $R_1$, $R_2$, $R_3$ and $R_4$ specified for the thiuram disulfide molecule may be the same or different. In the above formula, $R_1$, $R_2$, $R_3$ and $R_4$ are each independently selected from a set comprising hydrogen, alkyl, alkenyl, alkynyl, alkoxy, aryl and heteroaryl groups. In a specific embodiment, the alkyl group may be a linear, branched or cyclic $C_1$ to $C_{10}$ alkyl group, including a $C_1$ to $C_8$ alkyl group such as a $C_1$ to $C_6$ alkyl group, including $C_1$ to $C_4$ alkyl groups such as methyl, ethyl, propyl, isopropyl, n-butyl, isobutyl, tert-butyl, n-pentyl, isopentyl, neopentyl, cyclopropyl, cyclobutyl, cyclopentyl, cyclohexyl and cycloheptyl groups. The alkyl group may include cycloalkyl and heterocycloalkyl groups such as a cyclopropyl group, cyclobutyl group, etc. In a specific embodiment, the alkenyl group may be a $C_2$ to $C_{10}$ alkenyl group, including a $C_2$ to $C_8$ alkenyl group, such as a $C_2$ to $C_6$ alkenyl group, including a $C_2$ to $C_4$ alkenyl group, such as vinyl, propylene or butenyl. In a specific embodiment, the alkynyl group may be a $C_2$ to $C_{10}$ alkynyl group, including a $C_2$ to $C_8$ alkynyl group, such as a $C_2$ to $C_6$ alkynyl group, including a $C_2$ to $C_4$ alkynyl group, such as ethynyl, propynyl or butynyl. In a specific embodiment, the alkoxy group may be a $C_2$ to $C_{10}$ alkoxy group, including a $C_2$ to $C_8$ alkoxy group, such as a $C_2$ to $C_6$ alkoxy group, including a $C_2$ to $C_4$ alkoxy group such as methoxy, ethoxy, propoxy, n-butoxy, isobutoxy or tert-butoxy. In a specific embodiment, the aryl group may be a $C_6$ to $C_{14}$ monocyclic or bicyclic aromatic group such as a phenyl group, a fluorenyl group, etc., which may optionally further bear a substituent such as a benzyl group, etc. In a specific embodiment, the heteroaryl group is an aromatic group containing one or two heteroatoms independently selected from a set comprising nitrogen, oxygen and sulfur, such as a furyl, thienyl, pyrrolyl, thiazolyl, imidazolyl, pyridyl, pyrazinyl, pyrimidinyl or pyridazinyl group. In a specific embodiment, $R_1$, $R_2$ and N as well as $R_3$, $R_4$ and N may form a nitrogen-containing heterocycloalkane or a heterocyclic aromatic hydrocarbon. In some embodiments, $R_1$, $R_2$, $R_3$ and $R_4$ are each independently selected from a set comprising imidazolinyl, dimethylidene, bisphenol, cyclopropylmethyl, pentamethylene, hydroxyethyl and methyl glucosamine. In the case of disulfiram, $R_1$, $R_2$, $R_3$ and $R_4$ all correspond to ethyl.

The term "derivatives of disulfiram" includes compounds corresponding to the above formula, metabolites thereof, and salts thereof formed with sodium ions, potassium ions, ammonium ions, etc., as well as chelates formed with copper, zinc, iron, gold, and other divalent transition metals, such as DDC-Cu, DDC-Zn, etc.

In a particular embodiment of the present invention, "derivatives of disulfiram" include diethyl dithioate metabolites of disulfiram such as diethyldithiocarbamic acid (DDC) and salts thereof formed with sodium ions, potassium ions, ammonium ions, etc., as well as chelates formed with copper, zinc, iron, gold, and other divalent transition metals, such as DDC-Cu, DDC-Zn, etc.

Typical examples of disulfiram derivatives include: diethyldithiocarbamate or diethyldithiocarbamic acid (DDC), sodium diethyldithiocarbamate (DDC-Na), ammonium diethyldithiocarbamate (DDC-NH$_3$), copper diethyldithiocarbamate, zinc diethyldithiocarbamate, and other salts and chelates formed by diethyldithiocarbamic acid and other metal ions.

Coadministration with a Bivalent Transition Metal Preparation

For the purposes of the present invention, disulfiram or a derivative thereof may be administered alone or in conjunction with a divalent transition metal preparation to treat pleuroperitoneal membrane cancer.

According to a preferred embodiment of the present invention, a pharmaceutical preparation containing disulfiram or a derivative thereof constituted by the present invention (also referred to as a "pharmaceutical preparation constituted by the present invention") can be used in conjunction with a divalent transition metal preparation such as a copper-containing preparation, to thereby further enhance the anti-cancer efficacy of the treatment. The two formulations may be administered separately, simultaneously or sequentially. For example, disulfiram can be administered intraperitoneally while a copper-containing formulation such as copper gluconate is administered orally. Disulfiram and a copper-containing formulation can also be administered simultaneously or sequentially via intraperitoneal injection. The clinician can determine the dosage and mode of administration of the disulfiram and copper-containing preparations based on factors such as the state of the patient's disease as well as the patient's physical condition and response to the drug.

As used herein, "divalent transition metal preparation" refers to a substance or preparation containing a divalent transition metal element. As used herein, "bivalent transition metals" include copper, zinc, iron, gold, and other divalent transition metal elements. Typical examples of divalent transition metal preparations include copper-containing preparations and zinc-containing preparation. Examples of particularly suitable copper-containing preparations include copper gluconate, copper citrate, copper chloride, and other organic and inorganic copper preparations that are available for oral administration to patients. Examples of particularly suitable zinc-containing preparations include zinc gluconate, zinc chloride, zinc citrate, and other organic and inorganic zinc preparations that are available for oral administration to patients.

Combined Therapies

Many diseases can be treated with a combination of more than one drug, either administered simultaneously or sequentially. Accordingly, the present invention also encompasses the use of a pharmaceutical formulation constituted by the present invention in combination with other active agents conventionally used for the treatment of cancer to treat cancer.

For example, a preparation constituted by the present invention may be used in combination with surgery or radiation therapy, and/or in combination with one or more drugs, such as cumene, 5-fluorouracil, doxorubicin, paclitaxel, and gemcitabine.

Pharmaceutical Compositions

The present invention provides a pharmaceutical composition or pharmaceutical preparation comprising disulfiram or a derivative thereof as an active ingredient and a pharmaceutically acceptable carrier. A pharmaceutical composition constituted by the present invention can be used for treating thoracic and peritoneal cancer in a subject via intra-pleuroperitoneal administration.

A pharmaceutical composition constituted by the present invention may utilize a conventional pharmaceutically acceptable carrier or filler as well as other excipients such as cyclodextrin, sucrose, gelatin, magnesium stearate, olive oil, phospholipids, etc. For examples, see Remington: The Science and Practice of Pharmacy, 19th Edition, Gennaro, Ed., Mack Publishing Co., Easton, Pa., 1995.

Compounds constituted by the present invention can be prepared into a variety of suitable formulations, such as liquid injections, powders for injection, tablets for injection, or encapsulated in a liposome or other nano-excipient.

In general, the active ingredient included in a given preparation will account for approximately 0.005% to 95% by weight of the preparation with a range of 0.5% to 50% being preferable, depending on the mode of administration employed. The percentage of active compound included in a preparation will depend on the particular nature of the preparation, the activity of the compound and the needs of the patient. In a solution, the active ingredient will typically account for 0.01% to 90% of the total amount and if the preparation is obtained via solid dilution the content may be higher. In some embodiments, a liquid preparation will contain from 1% to 50% active compound.

Therapeutically Effective Dosage

As used herein, "therapeutically effective dose" refers to an amount of active compound that is sufficient to cause in the subject the biological or medical response desired by the clinician. A "therapeutically effective dose" of disulfiram or a derivative thereof can be determined by one skilled in the art based on factors such as the route of administration as well as the subject's weight, age, condition, etc.

In a preferred embodiment, said preparation will employ a unit dosage scheme. For example, the preparation can be placed in a vial or other container. The vial or other container may contain a liquid, solid to be diluted into a suspension, dry powder, lyophilizate, or any other preparation of a suitable form.

In some embodiments, disulfiram or a derivative thereof can be administered at a dose of approximately 250 to approximately 500 mg/day (the dose of disulfiram tolerated in patients undergoing alcoholic treatment ranges from 250 to 500 mg/day). The patient should preferably take 2 mg of copper, such as copper gluconate, simultaneously. Copper gluconate should preferably be administered orally.

In some embodiments, the disulfiram or derivative thereof can be administered with a dosage range of approximately 1 mg/kg to 10 mg/kg, with a range of approximately 1 mg/kg to 20 mg/kg being preferable. The disulfiram dose can also be calculated based on ascites volume on a basis of 10 micromoles of disulfiram per liter of ascites (2960 micrograms per liter). If the patient presents with 10 liters of ascites, the corresponding dose of disulfiram will be approximately 30 mg.

Kits

Another aspect of the present invention provides a kit comprising: (1) disulfiram or a derivative thereof as a therapeutic agent; and (2) instructions for use, wherein said instructions describe the use of disulfiram or a derivative thereof for the treatment of a subject's pleuroperitoneal membrane cancer via intra-pleuroperitoneal administration.

The kit constituted by the present invention is particularly well-suited to the treatment of pleuroperitoneal membrane metastatic cancer.

In the kit, disulfiram or a derivative thereof may be present in a unit dosage form, where the unit dose may be 10 mg/pcu. (e.g., 10 ml). The dose of the disulfiram or a derivative thereof may range from 1 to 10 mg/kg/day. A kit constituted by the present invention may also include an optional divalent transition metal preparation.

As used herein the term "optional" means "may or may not have" or "non-essential". For example, "optional copper preparation" means that a copper preparation may or may not be included, and a corresponding selection can be made by a person skilled in the art based on actual conditions.

In the following section, the present invention will be further described with reference to the included figures and examples, where said figures and examples are provided to illustrate the present invention and are not to be construed as limiting the scope of the present invention.

Example 1

Materials and Methods

MSTO, Ju77, 2591 and E58 mesothelioma cells were donated by Professor Peter Szlosarek of Queen Mary University of London and cultured in a DMEM medium containing 10% fetal calf serum supplemented with 10 mg/ml streptomycin and 2 mmol/L L-glutamine at 37° C. under a 5% $CO_2$ atmosphere. Separate incubations were performed with pemetrexed, DS/Cu (disulfiram/copper gluconate) and cisplatin for 3 days. Cell survival was determined via an MTT assay.

Results

Figure 1:
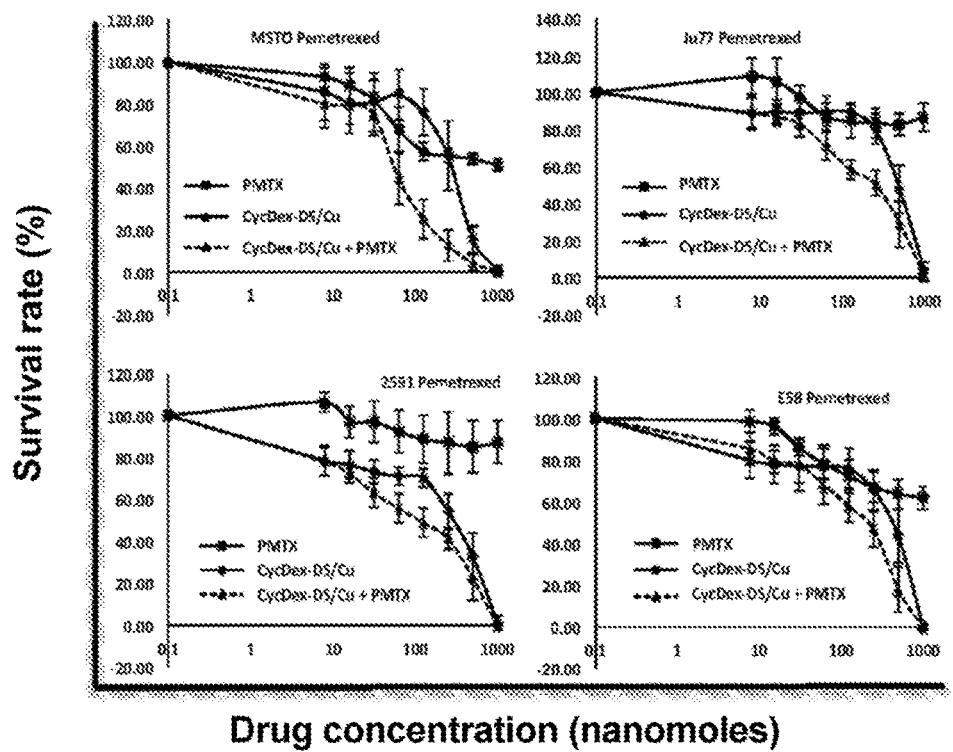
FIG. 1 shows the inhibition of mesothelioma cells. The figure shows the survival of MSTO, Ju77, 2591 and E58 cells after 3 days of incubation with pemetrexed (PMTX), DS/Cu, and both, respectively. Incubation with DS/Cu or both agents produced inhibition of mesothelioma cells which was significantly higher than that produced by pemetrexed alone, and the effect of both was higher than DS/Cu alone.
Figure 2:
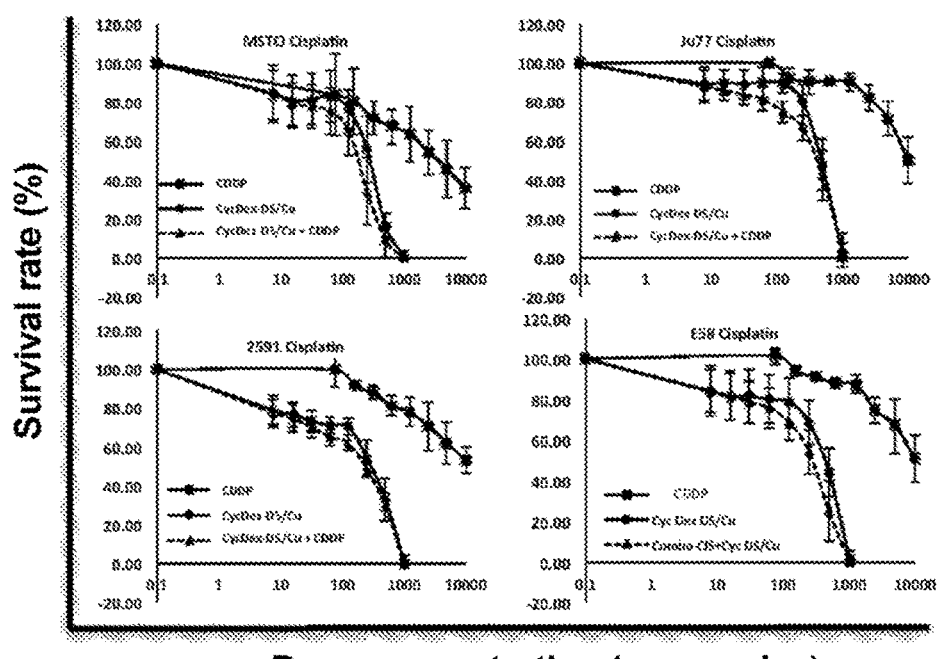
FIG. 2 shows the inhibition of mesothelioma cells. The figure shows the survival of MSTO, Ju77, 2591 and E58 cells after 3 days of incubation with cisplatin, DS/Cu, and both, respectively. Incubation with DS/Cu or both agents produced inhibition of mesothelioma cells which was significantly higher than that produced by cisplatin alone, and the effect of both was higher than DS/Cu alone.

Inhibition of mesothelioma cells by DS/Cu was significantly more pronounced compared to pemetrexed and cisplatin, and combined administration with the two drugs produced even better results (FIGS. 1 and 2, Tables 1 and 2).

Figure 3:
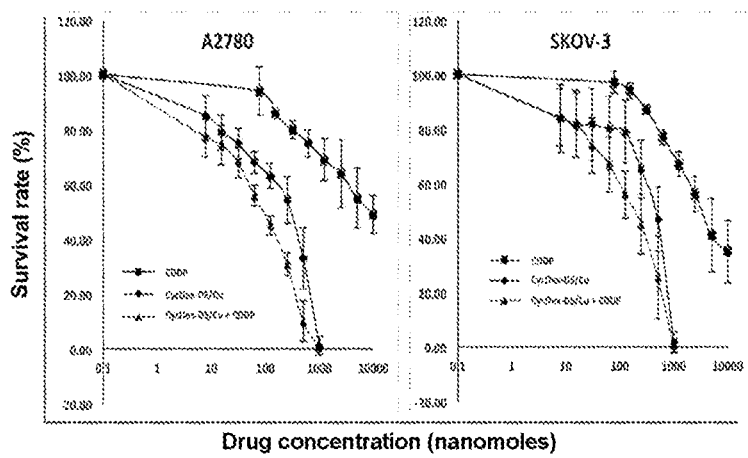
FIG. 3 shows the inhibition of ovarian cancer cells. The figure shows the survival of A2780 and SKOV-3 cells after 3 days of incubation with cisplatin, DS/Cu, and both, respectively. Incubation with DS/Cu or both agents produced inhibition of ovarian cancer cells which was significantly higher than that produced by cisplatin alone, and the effect of both was higher than DS/Cu alone.

Inhibition of human ovarian cancer cells by DS/Cu was also significantly more pronounced compared to cisplatin, and a significant synergistic effect with cisplatin was also observed (FIG. 3, Tables 3 and 4).

Example 2

Materials and Methods

S180 ascites cells were purchased from the Chinese Academy of Sciences Shanghai Cell Bank and cultured in a DMEM medium containing 10% fetal calf serum supplemented with 10 mg/ml streptomycin and 2 mmol/L L-glutamine at 37° C. under a 5% $CO_2$ atmosphere.

Animal Experiments

S-180 cells were injected at a rate of $2.5 \times 10^6$/animal into the abdominal cavity of male Kunming mice and the animals were randomly divided into two groups (8 animals/group). Beginning on the day after injection, mice in the control groups were orally and intraperitoneally injected with 0.1 ml of PBS, respectively while mice in the treatment group were orally administered 5 mg/kg of gluconate (CuGlu), followed by intraperitoneal injection of 5 mg/kg disulfiram 4 hours later. Drug administration was performed three times per week. The mice were weighed three times per week. Once the experiment was complete, the animals were sacrificed via cervical dislocation. The abdominal cavities of all mice were opened to observe and assess ascites formation and abdominal wall tumors. The liver, spleen, kidneys, lungs and other major organs were removed, embedded in paraffin, and sliced for HE staining.

Results

Figure 4:
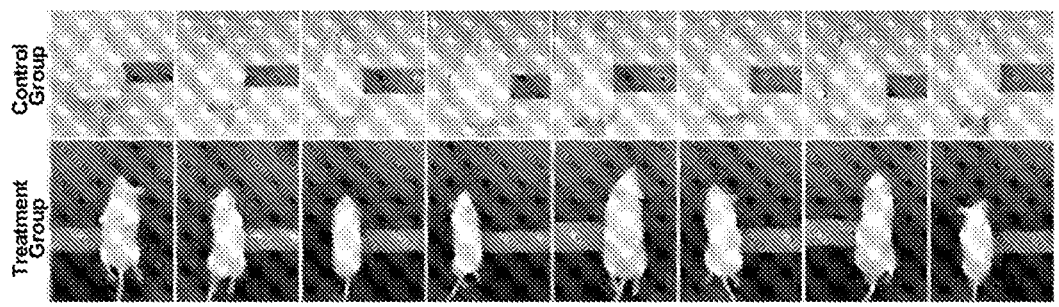
FIG. 4 shows the overall condition of experimental mice: after intraperitoneal injection of S-180 ascites tumor cells in BalB/C mice, the mice were generally in good condition during the test. Beginning on the third day after the injection (Day 3), the abdominal cavities of mice the control group gradually became larger, assuming a boat-like appearance on Day 7 and a spherical appearance on Day 11. The control group was sacrificed on Day 11. The treatment group was sacrificed after 21 consecutive days of observation. The control group showed abdominal distension while the treatment group was normal.
Figure 5:
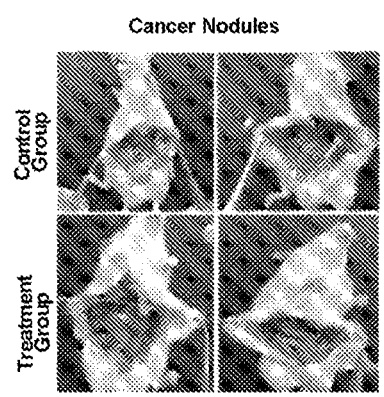
FIG. 5 shows a peritoneal cancer nodule. After intraperitoneal injection of ascites tumor cells in BalB/C mice, multiple cancer nodules were observed in the abdominal cavities of the control group on Day 11. The masses were clearly visible in the abdominal wall and mesentery, with 5 to 7 masses observed per animal, with diameters ranging from 0.2 to 1 cm. The treatment group was sacrificed on Day 21; the abdominal cavities of the mice were clean and no cancerous nodules were visible.
Figure 6:
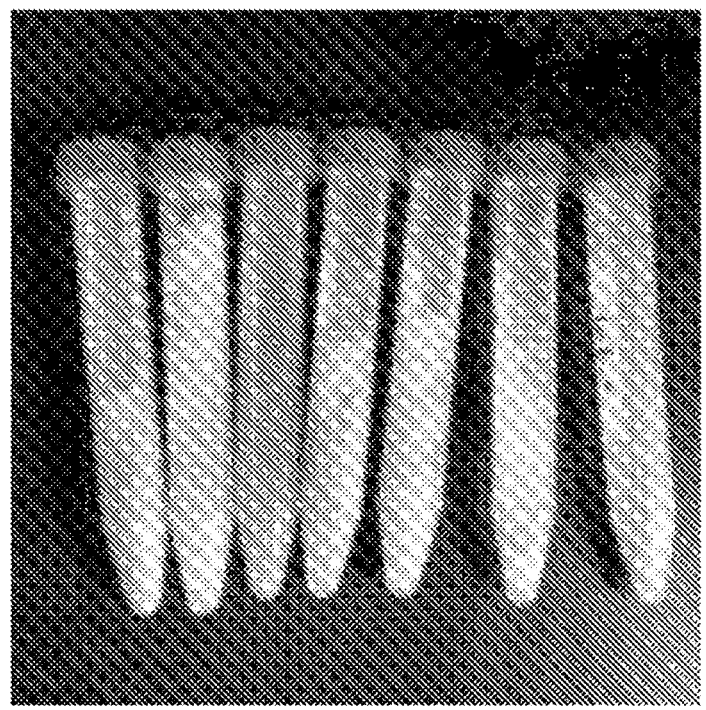
FIG. 6: After intraperitoneal injection of ascites tumor cells in BalB/C mice, on Day 11 mice in the control group were sacrificed, and a large amount of bloody ascites was observed in a laparotomy, at approximately 10 ml/animal. Ascites obtained from the control group are shown. The abdominal cavities of mice in the treatment group were completely normal and no ascites was observed.
Figure 7:
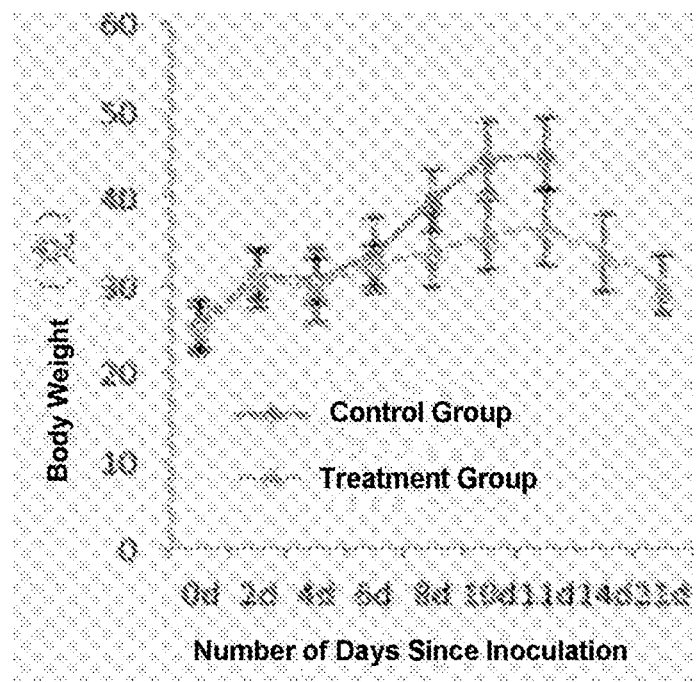
FIG. 7: Curve showing change in mouse body weight. After intraperitoneal injection of ascites tumor cells in BalB/C mice, the control group underwent a rapid increase in body weight due to the formation of cancer-related ascites. The treatment group showed a slight increase in body weight during the initial phase of the study, related to intra-abdominal cancer growth. After four days of treatment, weight gain in the treatment group plateaued, indicating that intraperitoneal cancer proliferation had been controlled by the drug administered. After 14 days the cancer cells were entirely killed due to the effect of the drug and the animals recovered to a normal by Day 21.
Figure 8:
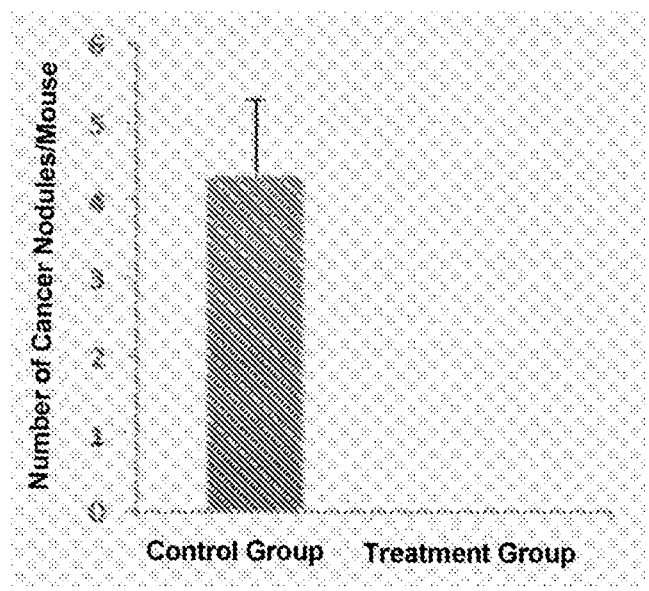
FIG. 8: Comparison of cancer nodule number. After intraperitoneal injection of ascites tumor cells in BalB/C mice, the average number of cancer nodules per mouse observed in the control group (Day 11) was significantly higher (P<0.01) than that observed in the treatment group (Day 21, 0 nodules per mouse).
Figure 9:
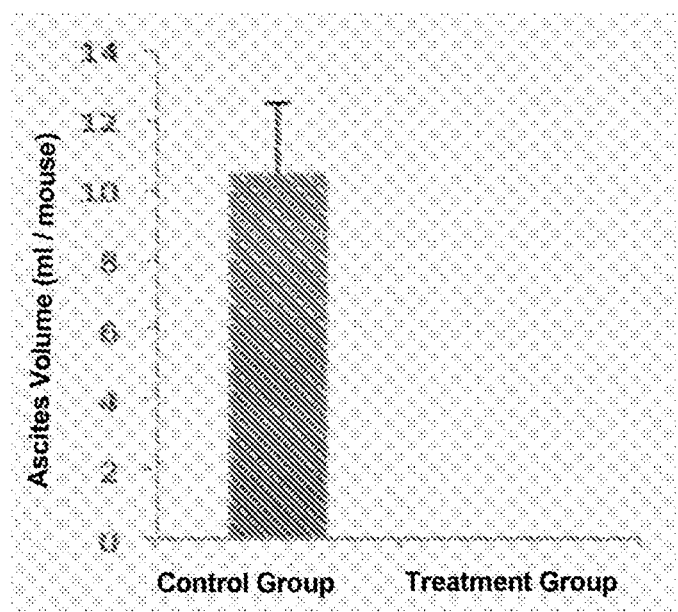
FIG. 9: Comparison of ascites volume. After intraperitoneal injection of ascites tumor cells in BalB/C mice, mean ascites volume (10 ml) per mouse observed in the control group (Day 11) was significantly greater (P<0.01) than in the treatment group (Day 21, 0 ml per mouse).
Figure 10:
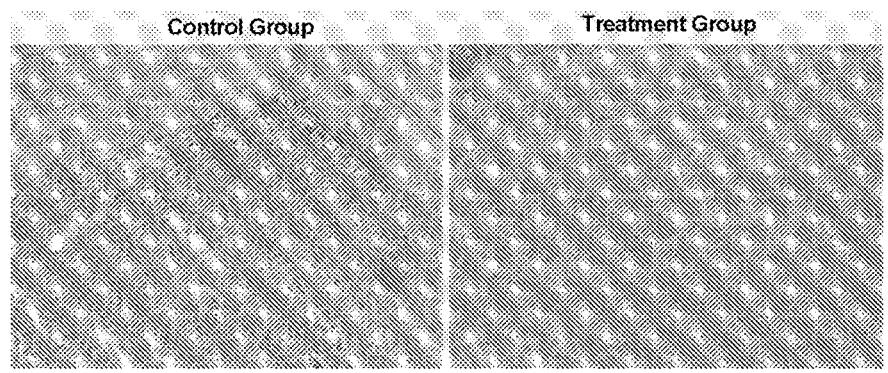
FIG. 10: Comparison of intra-abdominal invasion by cancer cells (100× magnification). After intraperitoneal injection of ascites tumor cells in BalB/C mice, cancer cells invaded the subserosal muscle layer of mice in the control group (Day 11). Blue arrow: cancer tissue; red arrow: muscle tissue. Mean ascites volume in the peritoneal cavity per mouse (10 ml) was significantly greater (P<0.01) than in the treatment group (Day 21, 0 ml per mouse). In the treatment group, muscle tissue was completely normal and no cancer cells were observed.
Figure 11:
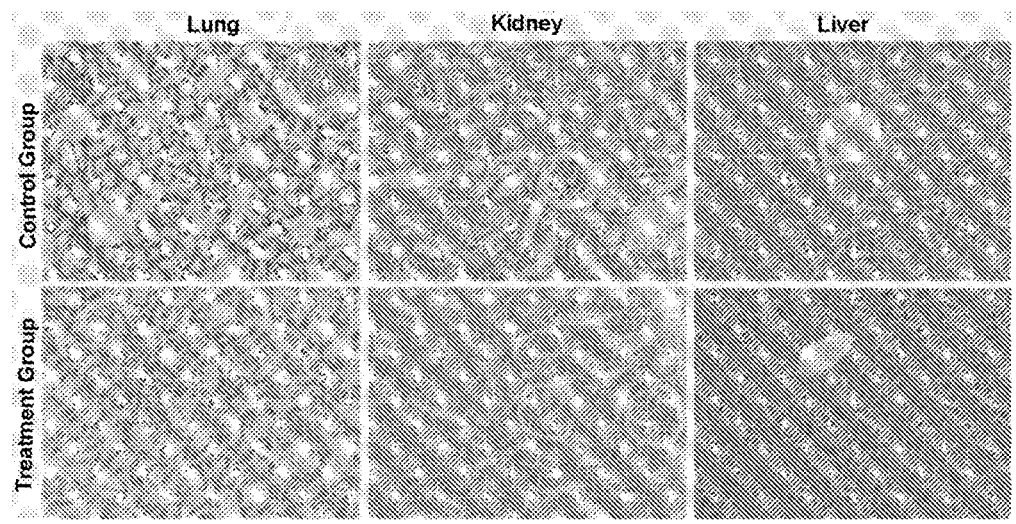
FIG. 11: Microscopic morphology of critical organs. After intraperitoneal injection of ascites tumor cells in BalB/C mice, no toxicity damage was observed in the critical organs (lung, kidney, liver) of mice in the control group (11 days) and the treatment group (21 days) (100× magnification).

During the course of the experiment, the mice were generally in good condition. Beginning on the third day after the injection (Day 3), the abdominal cavities of mice the control group gradually became larger, assuming a boat-like appearance on Day 7 and a spherical appearance on Day 11 (FIG. 4). One week after injection of the cells, the body weight of the mice in the treatment group was significantly lower than that of mice in the control group (FIG. 7). On Day 11, mice in the control group were sacrificed, and a large amount of bloody ascites was observed in a laparotomy, at approximately 10 ml/animal (FIG. 6). The masses were clearly visible in the abdominal wall and mesentery, with 5 to 7 masses observed per animal, with diameters ranging from 0.2 to 1 cm (FIGS. 5 and 8). HE staining confirmed said tumors were constituted by tumor tissue (FIG. 10). Three weeks after injection of the cells, mice in the treatment group were sacrificed, and no formation of ascites or masses was observed following laparotomy (FIG. 9). No significant lesions were found in vital organs such as the liver, spleen, kidneys and lungs (FIG. 11).

Example 3

Materials and Methods

MSTO mesothelioma cells and SKVO-3 ovarian cancer cells were cultured in a DMEM medium containing 10% fetal calf serum supplemented with 10 mg/ml streptomycin and 2 mmol/L L-glutamine at 37° C. under a 5% $CO_2$ atmosphere.

Animal Experiments

MSTO mesothelioma cells and SKVO-3 ovarian cancer cells were injected at a rate of $3 \times 10^6$/animal into female CD1 nude mice and animals were randomly divided into two groups (10 animals/group). Beginning on the day after injection, mice in the control group were intraperitoneally injected with 0.1 ml of PBS, while mice in the treatment group were orally administered 5 mg/kg of gluconate (Cu-Glu), followed by intraperitoneal injection of 40 µg/animal disulfiram 4 hours later. Drug administration was performed three times per week. The mice were weighed three times per week. Once the experiment was complete, the animals were sacrificed via cervical dislocation. The abdominal cavities of all mice were opened to observe and assess ascites formation and abdominal wall tumors.

Results

Figure 12:
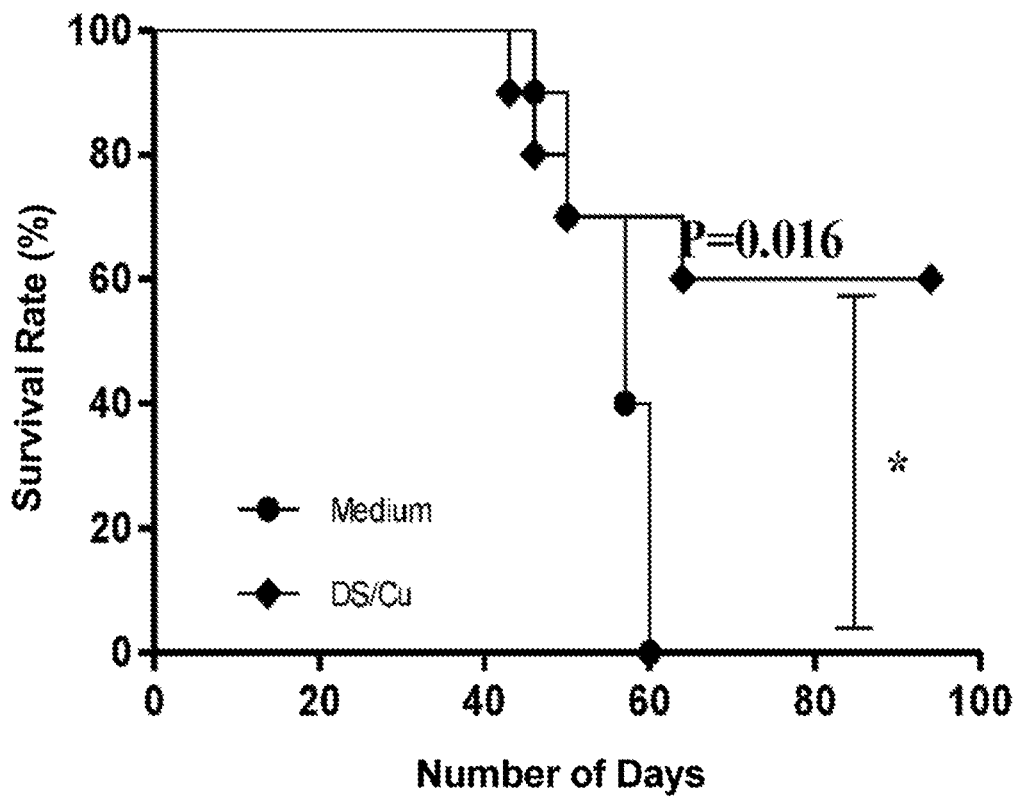
FIG. 12: This figure shows mouse survival. After CD1 nude mice were injected intraperitoneally with MSTO mesothelioma cells, all mice in the control group died by Day 60.

After injection of mesothelioma cells and ovarian cancer cells, all mice in the control groups died on Days 60 and 30, respectively (FIGS. 12 and 17), and a large amount of ascites was observed following laparotomy (FIGS. 13 and 18). A large number of masses were clearly visible in the abdominal wall, mesentery and liver (FIGS. 14, 15, 19 and 20). The survival rates of mice in the mesothelioma and ovarian cancer treatment groups on Days 90 and 60 were 60% and 90%, respectively (FIGS. 12 and 17). A laparotomy did not reveal any ascites, and only a small number of masses had formed (FIGS. 13 to 15 and 18 to 20).

DISCUSSION

Malignant pleuroperitoneal mesothelioma is the most common type of primary pleural tumor encountered in clinical practice. Clinical manifestations are associated with the tumor's invasive behavior as it locally invades the pleuroperitoneal cavity and surrounding structures. If the condition is left untreated, median survival is 4 to 12 months. Currently, there is no effective treatment for malignant pleuroperitoneal membrane mesothelioma available anywhere in the world. Pleuroperitoneal metastases were previously regarded as a terminal stage of cancer. The most common forms of pleuroperitoneal metastatic cancer include lung cancer, breast cancer, ovarian cancer, pancreatic cancer, liver cancer, stomach cancer, colorectal cancer, and any other cancer that metastasizes to the pleuroperitoneal membrane. Supportive care, systemic chemotherapy and palliative surgery are largely ineffective in extending patient survival.

Because malignant pleuroperitoneal membrane mesothelioma is mainly characterized by local invasive growth, it tends to produce less distal metastasis compared to other types of cancer. Intra-pleuroperitoneal administration of disulfiram is very likely to become an accepted method for treating pleuroperitoneal mesothelioma. For other pleuroperitoneal metastases, intraperitoneal application of disulfiram can inhibit abdominal metastasis and ascites formation in patients with cancer. Said treatment can effectively relieve symptoms and prolong survival. At present, the internationally recognized animal model of peritoneal metastasis involves injecting S180 ascites tumor cells into the peritoneal cavity of mice, inducing the mice to produce ascites and tumor nodules. In this study, we used the above model to evaluate the therapeutic effect of DS in the treatment of peritoneal metastasis. The control group which was not administered any drug showed a gradual increase in abdomen size two days after injection of tumor cells, accompanied by a rapid increase in body weight; laparotomy of animals sacrificed on Day 11 following cancer cell inoculation revealed the clear presence of tumor nodules. After animals in the Treated Group underwent three weeks of continuous administration, mice in the group administered DS via intraperitoneal administration showed no formation of ascites or tumor nodules, and no toxicity with respect to the primary organ systems was observed. This exciting result prompted the inventors of the present invention to further perform experiments pertaining to the treatment of peritoneal mesothelioma and ovarian cancer. In Example 3, the inventors of the present invention used only 1/20 of a typical dose of disulfiram used to treat alcoholism (2 mg/kg) to achieve 60% and 90% long term survival in peritoneal mesothelioma and ovarian cancer mice (90 and 60 days). In skin cancer studies, the inventors of the present invention administered drug to mice for three weeks after inoculation of the peritoneal cavity with mesothelial cancer cells, and the tumor-bearing mice produced ascites. Disulfiram was discontinued after only 6 weeks (12 administrations) and observation was continued for 4 weeks. 60% of mice achieved long-term survival (90 days). Thus, it can be inferred that intra-pleuroperitoneal administration of disulfiram is highly likely to become an accepted method for treating pleuroperitoneal mesothelioma.

Because disulfiram produces no systemic toxicity in either humans and animals, it can be administered over a long period of time. Based on the above, we can conclude that pleuroperitoneal injection of disulfiram has the ability to significantly inhibit the formation of pleuroperitoneal metastasis, prolonging the survival of animals and cancer patients and improving quality of life. Because copper, zinc and other divalent transition metal ions when combined with disulfiram can form DDC copper, zinc and other divalent transition metal ion derivatives (DDC-Cu, DDC-Zn, etc.) in the thoracic and peritoneal cavities and DDC-Cu is a very stable compound that can be absorbed into the bloodstream through the peritoneum, said combined therapy is effective for the treatment of primary cancer. Therefore, disulfiram has tremendous potential for research and development as a candidate for use in the treatment of pleuroperitoneal metastases.

TABLE 1

$IC_{50s}$ (nM) obtained for cisplatin (CDDP), pemetrexed (PMTX), and combined DS + Cu used to inhibit mesothelioma growth

|  | MSTO | Ju77 | E58 | 2591 |
| --- | --- | --- | --- | --- |
| CDDP | 4589 | 8792 | 8146 | 9155 |
| CDDP/DS + Cu | 154 | 366 | 268 | 192 |
| PMTX | 920 | >1000 | >1000 | >1000 |
| PMTX/DS + Cu | 62 | 238 | 194 | 114 |

TABLE 2

Synergistic effects of cisplatin (CDDP), pemetrexed (PMTX) and DS + Cu in the treatment of mesothelioma

|  | MSTO | Ju77 | E58 | 2591 |
| --- | --- | --- | --- | --- |
| CDDP |  |  |  |  |
| ED50 | 0.567 | 0.389 | 0.385 | 0.777 |
| ED75 | 0.320 | 0.346 | 0.355 | 0.868 |
| ED90 | 0.209 | 0.319 | 0.449 | 1.170 |
| PMTX |  |  |  |  |
| ED50 | 0.399 | 0.308 | 0.383 | 0.341 |
| ED75 | 0.196 | 0.431 | 0.384 | 0.253 |
| ED90 | 0.102 | 0.603 | 0.503 | 0.603 |

Synergy index CI: 0.9 to 1.1: Additive Effect; 0.8 to 0.9: Light; 0.6 to 0.8: Medium; 0.4 to 0.6: Synergistic; 0.2-0.4: Strong.

TABLE 3

$IC_{50s}$ (nM) of cisplatin (CDDP) alone as well as in combination with DS + Cu in the treatment of ovarian cancer cells

|  | A2780 | SKOV-3 |
| --- | --- | --- |
| CDDP | 4589 | 8792 |
| CDDP/DS + Cu | 154 | 366 |

TABLE 4

Synergistic effects of cisplatin (CDDP) and DS + Cu in suppressing ovarian cancer cell growth

|  | A2780 | SKOV-3 |
| --- | --- | --- |
| ED50 | 0.567 | 0.389 |
| ED75 | 0.320 | 0.346 |
| ED90 | 0.209 | 0.319 |

Synergy index CI: 0.9 to 1.1: Additive Effect; 0.8 to 0.9: Light; 0.6 to 0.8: Medium; 0.4 to 0.6: Synergistic; 0.2-0.4: Strong.

REFERENCES

AGARWAL, R. P., MCPHERSON, R. A. & PHILLIPS, M. 1983. Rapid degradation of disulfiram by serum albumin. Res Commun Chem Pathol Pharmacol, 42, 293-310.

AGARWAL, R. P., PHILLIPS, M., MCPHERSON, R. A. & HENSLEY, P. 1986. Serum albumin and the metabolism of disulfiram. Biochem Pharmacol, 35, 3341-7.

BRAR, S. S., GRIGG, C., WILSON, K. S., HOLDER, W. D., JR., DREAU, D., AUSTIN, C., FOSTER, M., GHIO, A. J., WHORTON, A. R., STOWELL, G. W., WHITTALL, L. B., WHITTLE, R. R., WHITE, D. P. & KENNEDY, T. P. 2004. Disulfiram inhibits activating transcription factor/cyclic AMP-responsive element binding protein and human melanoma growth in a metal-dependent manner in vitro, in mice and in a patient with metastatic disease. Mol Cancer Ther, 3, 1049-60. CEN, D., BRAYTON, D., SHAHANDEH, B., MEYSKENS, F. L., JR. & FARMER, P. J. 2004. Disulfiram facilitates intracellular Cu uptake and induces apoptosis in human melanoma cells. J Med Chem, 47, 6914-20.

CHEN, D., CUI, Q. C., YANG, H. & DOU, Q. P. 2006. Disulfiram, a clinically used anti-alcoholism drug and copper-binding agent, induces apoptotic cell death in breast cancer cultures and xenografts via inhibition of the proteasome activity. Cancer Res, 66, 10425-33.

GESSNER, T. & JAKUBOWSKI, M. 1972. Diethyldithiocarbamic acid methyl ester. A metabolite of disulfiram. Biochem Pharmacol, 21, 219-30.

ILJIN, K., KETOLA, K., VAINIO, P., HALONEN, P., KOHONEN, P., FEY, V., GRAFSTROM, R. C., PERALA, M. & KALLIONIEMI, O. 2009. High-throughput cell-based screening of 4910 known drugs and drug-like small molecules identifies disulfiram as an inhibitor of prostate cancer cell growth. Clin Cancer Res, 15, 6070-8.

JOHANSSON, B. 1992. A review of the pharmacokinetics and pharmacodynamics of disulfiram and its metabolites. Acta Psychiatr Scand Suppl, 369, 15-26.

KASLANDER, J. 1963. Formation of an S-glucuronide from tetraethylthiuram disulfide (Antabuse) in man. Biochim Biophys Acta, 71, 730-1.

LIU, P., BROWN, S., GOKTUG, T., CHANNATHODIYIL, P., KANNAPPAN, V., HUGNOT, J. P., GUICHET, P. O., BIAN, X., ARMESILLA, A. L., DARLING, J. L. & WANG, W. 2012. Cytotoxic effect of disulfiram/copper on human glioblastoma cell lines and ALDH-positive cancer-stem-like cells. Br J Cancer, 107, 1488-97.

LIU, P., WANG, Z., BROWN, S., KANNAPPAN, V., TAWARI, P. E., JIANG, J., IRACHE, J. M., TANG, J. Z., ARMESILLA, A. L., DARLING, J. L., TANG, X. & WANG, W. 2014. Liposome encapsulated Disulfiram inhibits NFκB pathway and targets breast cancer stem cells in vitro and in vivo. Oncotarget, 5, 7471-85.

PRICKETT, C. S. & JOHNSTON, C. D. 1953. The in vivo production of carbon disulfide from tetraethylthiuramdisulfide(antabuse). Biochim Biophys Acta, 12, 542-6.

STEWART, D. J., VERMA, S. & MAROUN, J. A. 1987. Phase I study of the combination of disulfiram with cisplatin. Am J Clin Oncol, 10, 517-9.

TAWARI, P. E. W., Z.; NAJLAH, M.; TSANG, C. W.; KANNAPPAN, V.; LIU, P.; MCCONVILLE, C.; HE, B.; ARMESILLA, A. L.; WANG, W. 2015. The cytotoxic mechanisms of disulfiram and copper (II) in cancer cells. Toxicology Research, 4, 1439-42.

VERMA, S., STEWART, D. J., MAROUN, J. A. & NAIR, R. C. 1990. A randomized phase II study of cisplatin alone versus cisplatin plus disulfiram. Am J Clin Oncol, 13, 119-24.

WANG, W., MCLEOD, H. L. & CASSIDY, J. 2003. Disulfiram-mediated inhibition of NF-kappaB activity enhances cytotoxicity of 5-fluorouracil in human colorectal cancer cell lines. Int J Cancer, 104, 504-11.

YIP, N. C., FOMBON, I. S., LIU, P., BROWN, S., KANNAPPAN, V., ARMESILLA, A. L., XU, B., CASSIDY, J., DARLING, J. L. & WANG, W. 2011. Disulfiram modulated ROS-MAPK and NFkB pathways and targeted breast cancer cells with cancer stem cell like properties. Br J Cancer, 104, 1564-74.

The invention claimed is:

1. A method of treating pleuroperitoneal membrane cancer which includes the intrapleural and/or intraperitoneal administration of an effective dose of disulfiram or a derivative thereof to a subject requiring treatment, wherein said derivative of disulfiram is selected from the group consisting of diethyldithiocarbamic acid, sodium diethyldithiocarbamate, ammonium diethyldithiocarbamate, copper diethyldithiocarbamate, and zinc diethyldithiocarbamate.

2. The method as claimed in claim 1, wherein said pleuroperitoneal membrane cancer corresponds to primary pleuroperitoneal membrane cancer.

3. The method as claimed in claim 2, wherein said primary pleuroperitoneal membrane cancer corresponds to malignant mesothelioma in the thoracic cavity and/or abdominal cavity.

4. The method as claimed in claim 1, wherein said primary pleuroperitoneal membrane cancer corresponds to pleuroperitoneal membrane metastasis.

5. The method as claimed in claim 1, which also includes the administration of a bivalent transition metal preparation either simultaneously or sequentially.

6. The method as claimed in claim 5, wherein said divalent transition metal preparation is a copper containing preparation or a zinc containing preparation.

7. The method as claimed in claim 6, wherein the said copper containing formulation is selected from a set comprising copper gluconate, copper citrate, and copper chloride.

8. The method as claimed in claim 6, wherein said zinc containing formulation is selected from a set comprising zinc gluconate, zinc chloride, and zinc citrate.

9. The method as claimed in claim 1, wherein said disulfiram or derivative thereof is administered at a dose of 1 mg/kg to approximately 10 mg/kg.

10. The method as claimed in claim 1, wherein said disulfiram or derivative thereof is administered in conjunction with another anti-cancer drug to treat the subject.

* * * * *